(12) United States Patent
Seemayer et al.

(10) Patent No.: US 6,911,544 B2
(45) Date of Patent: Jun. 28, 2005

(54) PROCESS FOR THE PREPARATION OF (S,S)-CIS-2-PHENYL-3-AMINOPIPERIDINE

(75) Inventors: Robert Seemayer, Palo Alto, CA (US); Thomas C. Nugent, San Francisco, CA (US); Jack Liang, Mountain View, CA (US)

(73) Assignees: Pfizer Inc., New York, NY (US); DSM Pharmaceuticals, Inc., Greenville, NC (US)

(*) Notice: Subject to any disclaimer, the term of this patent is extended or adjusted under 35 U.S.C. 154(b) by 0 days.

(21) Appl. No.: 10/682,313

(22) Filed: Oct. 9, 2003

(65) Prior Publication Data

US 2004/0110953 A1 Jun. 10, 2004

Related U.S. Application Data

(60) Provisional application No. 60/420,524, filed on Oct. 23, 2002.

(51) Int. Cl.$^7$ .......................................... C09D 211/52
(52) U.S. Cl. ..................................... 546/223; 546/192
(58) Field of Search ................................ 546/223, 192

(56) References Cited

U.S. PATENT DOCUMENTS 4,902,719 A * 2/1990 Gerhart et al. ............... 514/564
5,364,943 A * 11/1994 Rosen et al. ................. 546/223

* cited by examiner

Primary Examiner—Cecilia J. Tsang
Assistant Examiner—Raymond Covington
(74) Attorney, Agent, or Firm—Ladas & Parry LLP

(57) ABSTRACT

The present invention is directed to a process for preparing (S,S)-cis-2-phenyl-3-aminopiperidine and (S,S)-cis-2-phenyl-3-tertbutoxycarbonylaminopiperidine.

32 Claims, No Drawings

PROCESS FOR THE PREPARATION OF (S,S)-CIS-2-PHENYL-3-AMINOPIPERIDINE

This application claims the benefit of U.S. Provisional Application No.: 60/420,524 filed Oct. 23, 2002 and incorporates the same by reference.

FIELD OF THE INVENTION

The present invention relates to the method for the preparation of the title compound, (S,S)-cis-2-phenyl-3-aminopiperidine (1) and (S,S)-cis-2-phenyl-3-tert-butoxycarbonylaminopiperidine (1A), which are useful derivatives in the preparation of compounds that have utility as substance P antagonists.

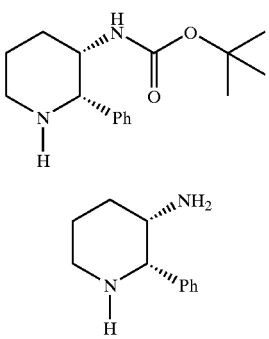

BACKGROUND OF THE INVENTION

Substance P is a naturally occurring undecapeptide belonging to the tachykinin family of peptides, members of which exert prompt stimulatory action on smooth muscle tissue. Substance P is a pharmaceutical active neuropeptide that is produced in mammals and possesses a characteristic amino acid sequence that is described in U.S. Pat. No. 4,680,283. A variety of substance P antagonists can be prepared from the title compound. For example, U.S. Pat. No. 5,323,929 describes Substance P antagonists of formula 2 where $R^1$ is a substituted or unsubstituted aryl, heteroaryl, or cycloalkyl group.

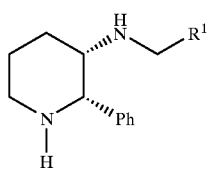

These antagonists can be prepared by reduction of 2-phenyl-3-aminopyridine followed by the reductive amination of the resulting 2-phenyl-3 aminopiperidine using the appropriate aldehyde of formula $R^1CH_2CHO$. Alternatively, these substance P antagonists can be obtained by reacting 2-phenyl-3-aminopyridine with a compound of the formula $R^1CH_2X$ where X is a leaving group to produce the pyridine analog of the substance antagonist. The pyridine analog is then reduced to obtain the final product.

Additional substance P antagonists that can be prepared from 2-phenyl-3-amino piperidine are described in U.S. Pat. No. 5,773,450, and PCT Applications WO 97/08144 and WO 01/77100. Methods employing 2-phenyl-3-amino piperidine to make substance P are also described in U.S. Pat. No. 5,232,929. The conventional method employed to prepare 2-phenyl-3-amino piperidine is described by Miller and Farrell (Tetrahedron Letters, 1998, 39, 6441–6444), is sensitive to air and results in a relatively low yield. In many cases, a late stage resolution has to be undertaken to obtain the active isomer, as for example, see Eur. Pat. Appl 1095939. The cis configuration of the amino and phenyl substituents is accessible by catalytic hydrogenation of the appropriately substituted pyridine compound as described in WO 92/17449, WO 93/01170 and U.S. Pat. No. 5,686,615. However, this method provides the racemic material which then has to be resolved as described in WO 94/27966.

A racemic analog of the desired amine has been prepared by a nitroaldol reaction followed by conversion of the trans-nitro compound to the cis amino compound by a Nef reaction followed by reduction of the oxime (see WO 93/01170 and Tetrahedron Letters, 1993, 34, 5831; a related reaction is given in Synthesis 1976, 615 and Journal of Prak Chemistry 1975, 317, 919).

A synthesis of 2 has been described from (S)-N,N-dibenzyl-O-tert-butyldimethylserinol (Tetrahedron Letters, 1999, 40, 5071) but the sequence involves nine steps. The key cyclization involves a displacement reaction. Phenylglycine methyl ester has also been used as the starting material to prepare an analogue of 2 (Synthesis, 1997, 475), with a 4-isopropyl substituent. In this case, the carboxylic acid provides an alcohol which is then substituted for the 3-amino group. A 4-substituent is necessary as the key cyclization step is an ene reaction.

Alkylation of (4R)-4-phenyl-2-azetidinone with 1-bromo-3-chloropropane followed by hydrolysis of the lactam and cyclization resulted in formation of a cis-piperidine derivative, but then a four step sequence was required to stereoselectively convert the carbomethoxy group to amino (see WO 93/01170 and Journal of Medicinal Chemistry 1992, 35, 4911).

Ornithine has been used to prepare piperidinones where homologation was performed with the lithium enolate of ethyl acetate. Removal of the protecting Cbz group by hydrogenolysis and in situ reduction of the imine led to the trans-product as summarized in Scheme 1 (Tetrahedron Letters 1993, 34, 3593 and 1992, 32, 1089; Journal of Medicinal Chemistry, 1997, 40, 3402).

Scheme 1:

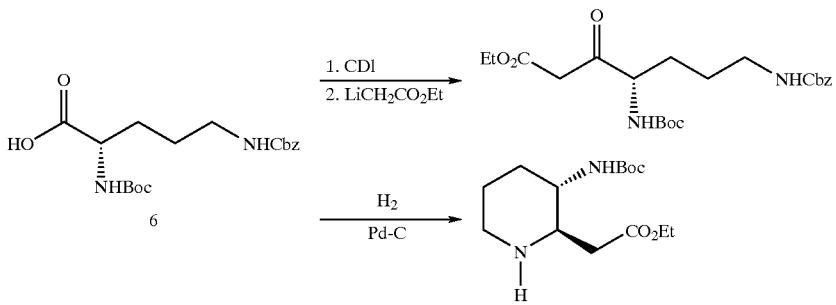

Reduction of the azide group in (S)-5-azido-2-hydroxy-1-phenyl-1-pentanone resulted in formation of a 4:1 mixture of the cis/trans 3-hydroxy-2-phenylpiperidine (Heterocycles 1999, 51, 1067).

SUMMARY OF THE INVENTION

The present invention relates to a simpler process for the preparation of (S,S)-cis-2-phenyl-3-tert-butoxycarbonylamino piperidine (1) and (S,S)-cis-2-phenyl-3-tert-butoxycarbonylaminopiperidines (1A), which is outlined hereinbelow in Scheme II. The invention relates to a process starting from the chiral material, L-ornithine (3) or a salt thereof. This amino acid, used preferably as a salt, especially as its hydrochloride salt (4) is selectively protected on the side chain amine on the δ-carbon and on the α-carbon, the two protecting groups being different and capable of being removed under different conditions. Preferably, the amine on the δ carbon is protected by an amine protecting group that can be removed by hydrogenolysis such as benzyloxycarbonyl or dithiasuccinoyl and the like. It is preferred that the protecting group of the amine on the δ carbon is protected with a benzyloxycarbonyl (Cbz) group in the presence of copper sulfate to complex the 2-amino carboxylate functionality. Following the hydrolysis of the copper complex to give 5, the amine on the α-carbon is protected with a second protecting group known in the art such as, for example, tert-butoxycarbonyl (Boc) group, to afford the differentially diprotected amino compound 6. The carboxylic acid of 6 is then transformed into the N-methoxy-N-methyl amide 7 commonly referred to as a Weinreb amide. Treatment of intermediate 7 with phenyl magnesium halide, e.g., chloride provides 8. Hydrogenation to remove the Cbz group permits internal cyclization to form the imine, reduction of the intermediate cyclic imine provides the desired compound 1 in excellent overall yield with no resolution required since the L-ornithine is chiral. Excellent diastereoselectivity for the required cis-stereochemistry is also observed.

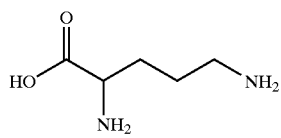

ornithine

Scheme II

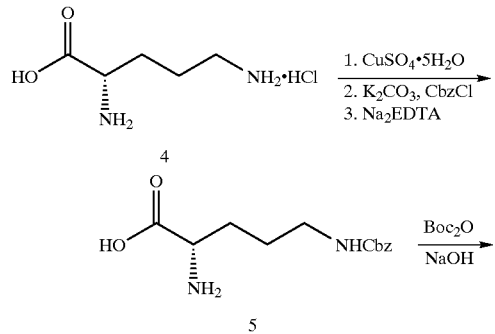

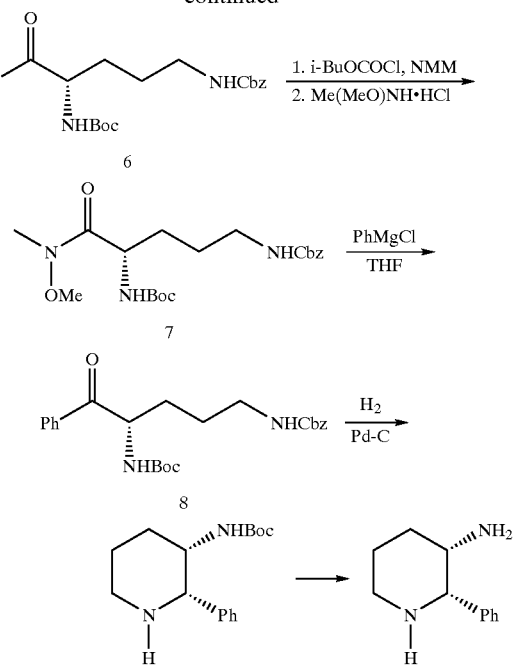

DETAILED DESCRIPTION

For those skilled in the art, there are many possible variations in the step sequence and protection group choice. The example that follows herein is intended as an illustration of a certain preferred embodiment of the invention, and no limitation of the invention is implied.

The invention is the synthesis of (S,S)-cis-2-phenyl-3aminopiperidine (1) as a single optical isomer from the readily available, natural amino acid L-ornithine (2). The preferred process is described herein.

In one aspect of the above-described method, the invention involves the following steps: Step one: Reaction of L-ornithine or salt thereof e.g., hydrochloride salt 4 with a protecting group. It is preferred that the L-ornithine or salt thereof, is reacted with copper sulfate pentahydrate under conditions effective to form a complex between the metal ion and the α-amino carboxylic acid moiety. This is followed by the reaction with Cbz chloride in the presence of a base to protect the δ-amino group.

Ethylenediaminetetraacetic acid (EDTA) disodium salt is used to de-complex the copper and provide compound 5 in 85–97% yield. Suitable bases include, but are not limited to, triethylamine, diisopropylethylamine, 2,6-lutidine, N,N,N', N'-tetramethylethylenediamine, potassium carbonate, sodium carbonate, lithium carbonate, sodium hydroxide and potassium hydroxide. Potassium carbonate is the preferred base for this reaction. Solvents for these reactions include alcoholic solvents, water, or a mixture of alcoholic solvents and water. The preferred solvent for this reaction is water. The product 5 is isolated as a solid, and it was used without any further purification.

Step two of this scheme involves the protection of the second amino group of the isolated intermediate 5 from step 1, using art recognized amine protecting groups. Preferably, intermediate 5 is reacted with a base and di-t-butyl dicarbonate (Boc anhydride) to form intermediate 6. Suitable bases for this reaction include, but are not limited to, sodium carbonate, sodium bicarbonate, potassium carbonate, potassium hydroxide, sodium hydroxide, potassium fluoride, and barium hydroxide. Solvents for these reactions include alcoholic solvents, water, or a mixture of alcoholic solvents and water. In one embodiment of step 2, the reaction is carried out in aqueous sodium hydroxide solution with di-t-butyl dicarbonate and 6 is isolated by extraction with ethyl acetate. A slight excess of Boc anhydride relative to intermediate 5 was found to be advantageous for high yield; preferably it is present between 1.2 and 3.0 equivalents per each equivalent of intermediate 5. The preferred amount of Boc anhydride is 2 equivalents relative to intermediate 5.

Step three of this scheme involves the formation of the Weinreb amide 7. The intermediate 6 from the previous reaction is treated with an agent to make the aryl group on intermediate 6 more active, such as a group converting the acid to an acid halide, e.g., acid chloride or an ester or other group which is capable of reacting with an amide (activating agent), followed by the addition of N-methoxy-N-methyl-amine hydrochloride with the appropriate base and in an appropriate solvent. Appropriate solvents for the reaction could be any homogenate hydrocarbon such as methylene chloride, dichlorobenzene, chlorobenzene, dichloroethane, or other inert solvents such as THF or toluene, and the like. Suitable bases include, but are not limited to, triethylamine, diisopropylethylamine, 2,6-lutidine, N,N,N',N'-tetramethylethylenediamine, potassium carbonate, sodium hydroxide, potassium hydroxide, and N-methylmorpholine. The carboxylic acid activating agents can be an alkyl chloroformate such as methyl or ethyl or isobutyl chloroformate. Those skilled in the art will appreciate that other activation agents such as acid chlorides or carbodiimides could also be employed.

For example, one embodiment of step 3 is carried out in methylene chloride as a solvent and N-methylmorpholine as a base and isobutyl chloroformate as the activating agent. The reaction is preferably started at −20° but is typically run at room temperature. The product 7 is isolated by extractive work up with suitable solvents, most preferably ethyl acetate.

Step four is displacement of this newly generated Weinreb amide 7 with phenylmagnesium halide, e.g., chloride. The reaction is run under anhydrous conditions and an inert atmosphere. It is run in a suitable solvent for these types of reactions, which includes but is not limited to THF, methyl-THF, diethyl ether, diisopropyl ether, methyl-tert-butyl ether and toluene. Phenyl magnesium chloride was used; however, phenyl magnesium bromide or iodide can be used also.

To effect addition of the phenyl group to the Weinreb amide 7, it is preferred that at least three equivalents of the Grignard reagent are required as the substrate contains two acidic N—H groups. From 3–6 equivalents of the Grignard reagent is more preferred. In this embodiment, the most preferred amount is 4.0–4.5 equivalents.

Addition of a solution of phenylmagnesium halide, e.g., phenylmagnesium chloride, to a solution of the amide 7 results in cyclization involving the δ-carbamate group and formation of the corresponding lactam in a major reaction pathway. The preferred mode of addition is an "inverse" addition where a solution of the amide 7 is added to excess Grignard reagent.

The addition of the Weinreb amide to the phenylmagnesium chloride is controlled in order to maintain an internal temperature between −20° and +5° C. The reaction is quenched with ice and acid and the product 8 is extracted and isolated in the usual fashion.

Although a variety of inert solvents can be used in the transformation of 7 to 8, the reaction conditions have to be carefully controlled. When the amide 7 was added as a solution in 1,2-dimethoxyethane, then a substantial amount of over addition, that is formation of the diphenylcarbinol, was observed. In this embodiment, THF is the preferred solvent for the Grignard addition step.

Step five involves the hydrogenation of this intermediate 8 to remove the Cbz protecting group followed by the immediate cyclization and reduction to form the product 1. This reaction is run in an appropriate solvent which includes but is not limited to alcohol solvents such as methanol, ethanol and isopropanol or inert solvents such as THF, methyl-THF, ethyl acetate, diisopropyl ether, methyl-tert-butyl ether, toluene, methylene chloride, and mixtures thereof. The preferred catalyst for this transformation is palladium on carbon; the preferred hydrogen pressure is between 50 and 200 psi, most preferably 150 psi. The catalyst loading is anywhere between 1–10 mole percent but preferably 5 mole percent. The preferred solvent is methanol.

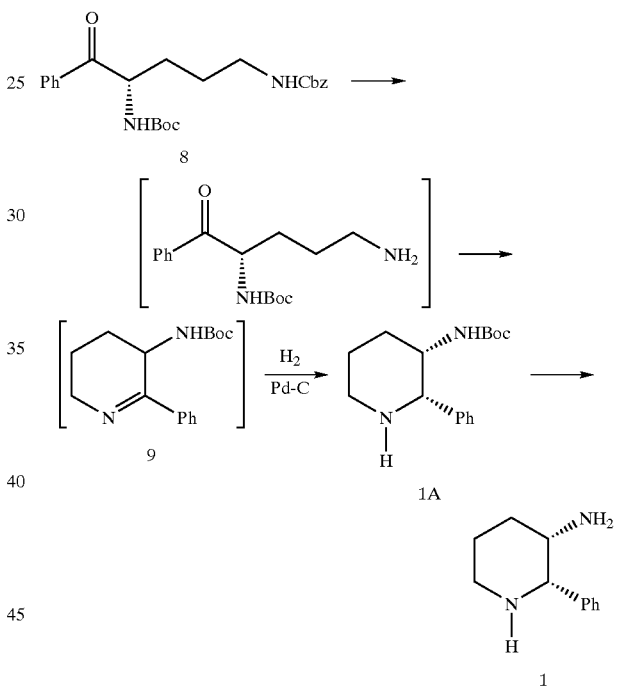

Finally, the remaining protecting group is removed by techniques known in the art to afford a compound of Formula I. Although alternative methods could be used to deprotect the δ-amino group, hydrogenolysis allows the imine 9, which formed by the cyclization of the free 8-amino group when it has been unmasked and the carbonyl moiety, to be reduced under the same reaction conditions. Those skilled in the art appreciate that deprotection, cyclization to the imine and subsequent reduction might be accomplished as separate, discrete steps and that alternative reagents, such as sodium cyanoborohydride for the imine reduction, could be employed. Compared to related processes, as described above, the formation of the cis isomer as the major product is a novel outcome. When the 2-substituent is not phenyl, the analogous reaction provides the trans-product where the substituents are in equatorial dispositions. When a 2-aryl substituent is present, the conjugation of the imine allows enough face selectivity to be exerted by the bulky 3-nitrogen group so that reduction occurs from the least hindered face to give the cis-product.

The above-described process of the present invention achieves a significant advantage over previous approaches as resolution is avoided by the use of L-ornithine, a cheap, readily available member of the chiral pool. Formation of the diastereoisomers and enantiomer of the desired product 1 is minimized. Access to 1 by a simple process allows access to a wide range of Substance P anatagonists in optically pure form.

The examples that follow are intended as illustrations of certain preferred embodiments of the invention, and no limitation of the invention is implied.

EXAMPLES (a) δ-N-Cbz L-Ornithine 5

To a flask under air was added L-ornithine.HCl (4) (16.9 g; 100 mmol) and 0.5N NaOH (200 mL; 100 mmol). To the resultant clear, colorless solution was added $CuSO_4.5H_2O$ (12.5 g; 50.0 mmol). After stirring for 15 min, $K_2CO_3$ (13.8 g; 100 mmol) was added followed by of Cbz-Cl (19 mL; 128 mmol). After stirring for 3 h, the purple precipitate was collected and rinsed with MeOH (2×50 mL). The purple precipitate was added to a solution containing EDTA (14.6 g; 50.0 mmol) in 0.25N NaOH (400 mL; 100 mmol). The resultant slurry was heated to 95° C. with vigorous stirring for 1 h then cooled to room temperature. The precipitate was collected and rinsed with $H_2O$ (2×100%). After air-drying overnight, 22.6 g (85% yield; typical yield is between 85–90%) of a pale blue solid as 5 was obtained and used without further purification.

(b) α-N-Boc δ-N-Cbz L-ornithine 6

To a flask under air was added 5 (22.6 g; 85.0 mmol) and 0.5N NaOH (170 mL; 85 mmol). A homogeneous solution was obtained after stirring for ~5 min. To this solution was added MeOH (170 mL) and $Boc_2O$ (37.1 g; 170 mmol). After stirring for 2 h, the white precipitate was filtered off and discarded and the solution was rotary evaporated to remove MeOH. The resultant aqueous solution was washed with EtOAc (2×250 mL). The pH of the aqueous solution was adjusted to ~2 with conc. HCl, then extracted with EtOAc (3×200 mL). The organic phase was combined and washed with sat. NaCl (200 mL). Heptane (100 mL) was added to the organic phase. The organic solvent was removed via vacuum to give 21.3 g of the acid 6 (68% yield; typical yield is between 68–85%) as a thick viscous oil and which was used without further purification. $^1$H-NMR (300 MHz, $d_6$-DMSO) δ 7.23–7.34 (m, 5H, $C_6H_5$), 7.16 (m, 1H, $NHCO_2R$), 6.96 (d, 1H, J=8.0, $NHCO_2R$), 4.97 (s, 2H, $PhCH_2$), 3.81 (m, 1H, α-H), 2.95 (m, 2H, $RCH_2NHCbz$), 1.63 (m, 1H), 1.43–1.53 (m, 3H), 1.41 (s, 9H, $C(CH_3)_3$).

(c) Weinreb Amide 7

To a flask under a nitrogen atmosphere was added the acid 6 (21.3 g; 58.2 mmol) and $CH_2Cl_2$(200 mL). The reaction mixture was cooled using a salt/ice bath. To the chilled reaction mixture was added N-methylmorpholine (NMM) (13.3 mL; 121 mmol). After 15 min, i-BuOCOCl (8.0 mL; 61.5 mmol) was added dropwise over 15 min, maintaining the internal temperature below −10° C., then the reaction mixture was maintained at −10° C. for an additional 30 min. Me(OMe)NH.HCl (7.85 g; 80.4 mmol) was next added. The reaction was allowed to warm to room temperature over 1 h and kept there for 3 h. The reaction mixture was poured into EtOAc (500 mL) and washed successively with 2N HCl (2×150 mL), sat. $NaHCO_3$ (2×150 mL) and sat. NaCl (15 mL). Heptane (200 mL) was added and the solvent removed by a rotatory evaporator at 50° C., to give the Weinreb amide 7 (22.2 g; 93% yield; typical yield is between 79–93%) as a viscous oil. $^1$H-NMR (300 MHz, $d_6$-DMSO) δ 7.24–7.55 (m, 5H, $C_6H_5$), 7.16 (m, 1H, $NHCO_2R$), 6.91 (d, 1H, J=8.0, $NHCO_2R$), 4.97 (s, 2H, $PhCH_2$), 4.32 (m, 1H, α-H), 3.57 (s, 3H), 3.03 (s, 3H), 2.94 (m, 2H, $RCH_2NHCbz$), 1.38–1.48 (m, 4H), 1.33 (s, 9H, $C(CH_3)_3$).

(d) 5-(Benzoylcarbonylamino)-2S-(tert-butoxycarbonylamino)-1-phenylpentan-1-one 8:

To a flask fitted with an addition funnel under a nitrogen atmosphere was placed 2M PhMgCl in THF (75 mL 150 mmol) and anhydrous THF (50 mL). The solution was cooled to 0° C. by an ice bath. To the addition funnel was added the Weinreb amide 7 (11.1 g; 27.1 mmol) in anhydrous THF (75 mL). The THF solution of 7 was added dropwise to the Grignard solution over ~30 min, maintaining the internal temperature between 3–4° C. After an additional 30 min, the reaction mixture was added to a slurry of ice (150 g) and of 2N HCl (150 mL). The mixture was stirred for ~5 minutes and then poured into i-PrOAc (600 mL). The organic phase was washed with sat. NaCl (200 mL). The solvent was removed and the residue passed through silica gel using 1:3 EtOAc/heptane. Following solvent strip, a viscous oil (8.52 g) was obtained which was slurried in i-PrOAc (9 mL) and heptane (81 mL), heated to 90° C. and then cooled to room temperature overnight with stirring. The white precipitate was collected, rinsed with heptane (2×20 mL) and air dried to give the phenyl ketone 8 (7.72 g; 67% yield; typical yield is between 48–67%; >99% ee). DSC indicates that the enantiopure phenyl ketone 8 has a m.p. of 86° C. $^1$H-NMR (300 MHz, $d_6$-DMSO) δ 7.95 (d, 2H, J=7.2, Ar—H), 7.62 (m, 11H, Ar—H), 7.52 (m, 2H, Ar—H), 7.24–7.35 (m, 7H, $C_6H_5$), 5.00 (s, 2H, $PhCH_2$), 4.93 (m, 1H, α-H), 3.00 (m, 2H, $RCH_2NHCbz$), 1.68 (m, 1H), 1.52–1.56 (m, 3H), 1.35 (s, 9H, $C(CH_3)_3$).

(e) (S,S)-Cis-2-Phenyl-3-(tert-butoxycarbonylamino) piperidine 1

To a 300-mL Parr reactor was added the phenyl ketone 8 (4.26 g; 10.0 mmol), anhydrous MeOH (50 mL) and 50% wet Englehard Escat10 5% Pd/C (420 mg; 0.10 mmol; 1 mol %). The glass liner was loaded into the reactor and stirred at 300 rpm. under 150 psig of $H_2$ at room temperature for 16 hours. The catalyst was filtered off and rinsed with MeOH (2×50 mL). The solvent was stripped by a rotatory evaporator and the crude product was passed through a plug of silica gel using 500 mL of 5:35:60 $NEt_3$/EtOAc/heptane. After solvent removal, 2.00 g (72% yield) of analytically pure 1 was obtained as a white solid: $^1$H-NMR (400 MHz, $C_6D_6$) δ 7.02–71.8 (m, 5H, $C_6H_5$), 5.46 (d, 1H, J=8.9, NHBoc), 4.15 (m, 11H, CHNHBoc), 3.46 (d, 1H, J=2.0, CHPh), 2.68 (ddd, 1H, J=8.8, 2.0, 2.0), 2.27 (ddd, 1H, J=11.3, 11.0, 3.0), 2.12 (m, 1H), 1.43–1.62 (m, 3H), 1.37 (s, 9H, $C(CH_3)_3$), 1.18 (m, 1H). A 20 mg sample was derivatized with (S)-(+)-1-(1-naphthyl)ethyl isocyanate for hplc analysis that showed the cis/trans ratio as 46:1 (97.9:2.1) and the cis diastereoisomer to have an optical purity of 93% ee.

What is claimed is:

1. A process for preparing (S,S)-cis-2-phenyl-3-aminopiperidine which comprises:
   (a) reacting the amino acid, L-ornithine or salt having a protecting group on the amino group on the α-carbon and the amino group on the δ-carbon thereof, having the formula

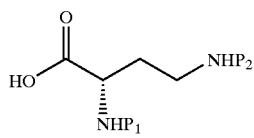

with N-methoxy-N-methylamino or salt thereof under amide forming conditions to produce an amide of the formula in the S configuration

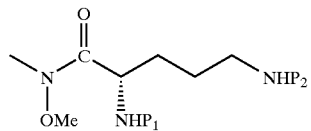

(b) adding said amide to an effective amount of a Grignard reagent of the formula Ph MgX to form a ketone of the formula in the S configuration

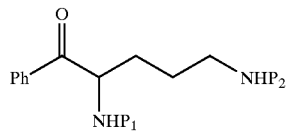

(c) selectively deprotecting the amino group on the δ carbon under conditions sufficient to cyclize said ketone to form a cyclic imine and reducing the resulting imine to form a product of the formula in the (S,S) configuration

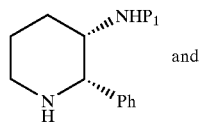

(d) removing the protecting group on the α-carbon to form said (S,S)-cis-2-phenyl-3-aminopiperidine, wherein $P_1$ and $P_2$ are different amino protecting groups, which are removed under different reaction conditions and X is halide.

2. The process according to claim 1 which additionally comprises differentially protecting the amino groups on the α and δ carbon atoms on the L-ornithine or salt thereof prior to step (a).

3. The process according to claim 2 wherein the amino group on the δ-carbon is protected by a group that can be removed by hydrogenolylsis.

4. The process according to claim 2 wherein the protecting group on the amino group on the δ-carbon is benzyloxycarbonyl or dithiasuccinoyl.

5. The process of claim 2 wherein differentially protecting the α and δ amino groups comprises:
   (a) reacting the L-ornithine with a copper salt to form a copper complex with the amino group on the α-carbon,
   (b) adding a protecting group to the amino group on the δ carbon,
   (c) de-complexing the copper, and
   (d) protecting the amino group on the α-carbon.

6. The process of claim 5 wherein the copper salt is copper sulfate pentahydrate.

7. The process of claim 1 wherein the amino group on the δ carbon is protected by benzyloxycarbonyl CBZ.

8. The process according to claim 1 wherein in step (a) base is additionally present.

9. The process according to claim 8 wherein the base is triethylamine, diisopropyl ethylamine, 2,6-lutidine, N,N,N', N'-tetramethylethylenediamine, potassium carbonate, lithium carbonate, sodium hydroxide, potassium hydroxide or N-methylmorpholine.

10. The process according to claim 1 wherein the Grignard reagent is phenyl magnesium bromide, phenyl magnesium chloride or phenyl magnesium iodine.

11. The process according to claim 1 wherein from 3–6 equivalents of Grignard reagent is used per amide.

12. The process according to claim 11 wherein about 4.0 to about 4.5 equivalents of Grignard reagent is used relative to the amide.

13. The process of claim 1 wherein the reduction of the cyclic imine is effected by catalytic hydrogenation.

14. The process of claim 13 wherein the catalyst is palladium on carbon.

15. The process of claim 13 wherein the reduction of the cyclic imine is conducted in a solvent and the solvent is methanol.

16. The process of claim 1 wherein the deprotection of the amino group on the δ carbon is performed at the same time as imine formation and reduction.

17. A process for preparing (S,S)-cis-2-phenyl-3-tertbutoxycarbonylaminopiperdine which comprises
   (a) reacting the amino acid, L-ornithine or salt thereof having a Boc protecting group on the amino group on the α-carbon and a protecting group on the amino group on the δ carbon thereof, having the formula:

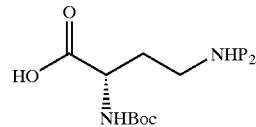

with N-methoxy-N-methylamino or salt thereof under amide forming conditions to produce an amide of the formula in the S configuration

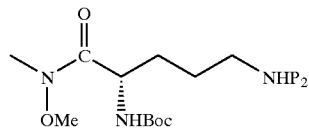

(b) adding said amide to an effective amount of a Grignand reagent of the formula Ph MgX to form a ketone of the formula in the S configuration

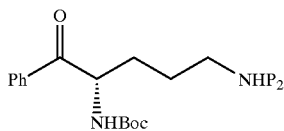

(c) selectively deprotecting the amino group on the δ carbon under conditions sufficient to cyclize said ketone to form a cyclic imine and reducing the resulting imine to form a product of the formula in the (S,S) configuration

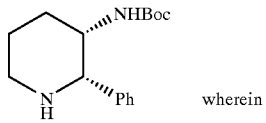

wherein $P_2$ is an amino protecting group other than Boc,
X is halide.

18. The process according to claim 17 wherein the amino group on the δ carbon is protected by a group that can be removed by hydrogenolylsis.

19. The process according to claim 17 wherein the protecting group on the δ amino group on the δ carbon is benzyloxycarbonyl.

20. The process of claim 17 wherein the L-ornithine compound or salt thereof of the formula

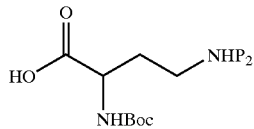

is prepared by
(a) reacting the L-ornithine with a copper salt to form a copper complex with the amino group on the α-carbon,
(b) adding a protecting group to the amino group on the δ carbon,
(c) de-complexing the copper, and
(d) reacting the product of (c) with Boc anhydride in the presence of an inorganic base.

21. The process of claim 20 wherein the copper salt is copper sulfate pentahydrate.

22. The process of claim 20 wherein the amino group on the δ carbon is protected by CBZ.

23. The process according to claim 1 wherein in step (a) base is additionally present.

24. The process according to claim 23 wherein the base is triethylamine, diisopropyl ethylamine, 2,6-lutidine, N,N,N', N'-tetramethylethylenediamine, potassium carbonate, lithium carbonate, sodium hydroxide, potassium hydroxide or N-methylmorpholine.

25. The process according to claim 17 wherein the Grignard reagent is phenyl magnesium bromide, phenyl magnesium chloride or phenyl magnesium iodine.

26. The process according to claim 17 wherein from 3–6 equivalents of Grignard reagent is used per amide.

27. The process according to claim 26 wherein about 4.0 to about 4.5 equivalents of Grignard reagent is used relative to the amide.

28. The process of claim 17 wherein the reduction of the cyclic imine is effected by catalytic hydrogenation.

29. The process of claim 28 wherein the catalyst is palladium on carbon.

30. The process of claim 28 wherein the reduction of cyclic imine is conducted in a solvent and the solvent is methanol.

31. The process of claim 17 wherein the deprotection of the amino group on the δ carbon is performed at the same time as imine formation and reduction.

32. The process according to claim 20 wherein the inorganic base is sodium carbonate, sodium bicarbonate, potassium carbonate, potassium hydroxide, sodium hydroxide, potassium fluoride or barium hydroxide.

* * * * *

UNITED STATES PATENT AND TRADEMARK OFFICE
CERTIFICATE OF CORRECTION

PATENT NO.     : 6,911,544 B2
DATED          : June 28, 2005
INVENTOR(S)    : Robert Seemayer et al.

It is certified that error appears in the above-identified patent and that said Letters Patent is hereby corrected as shown below:

Title page,
Item [*] Notice, "0" should read -- 77 --.

Signed and Sealed this

Twentieth Day of September, 2005

JON W. DUDAS
*Director of the United States Patent and Trademark Office*